United States Patent
Lotfallah et al.

(10) Patent No.: US 11,540,203 B2
(45) Date of Patent: Dec. 27, 2022

(54) TECHNIQUES FOR USER EQUIPMENT (UE) DYNAMICALLY ADJUSTING A NON-ACCESS STRATUM (NAS) TIMER IN A WIRELESS COMMUNICATION SYSTEM

(71) Applicant: QUALCOMM Incorporated, San Diego, CA (US)

(72) Inventors: Osama Lotfallah, San Diego, CA (US); Amer Catovic, San Diego, CA (US); Liangchi Hsu, San Diego, CA (US); Lenaig Genevieve Chaponniere, La Jolla, CA (US); Arvind Vardarajan Santhanam, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 17/232,041

(22) Filed: Apr. 15, 2021

(65) Prior Publication Data

US 2021/0329536 A1    Oct. 21, 2021

Related U.S. Application Data

(60) Provisional application No. 63/011,968, filed on Apr. 17, 2020.

(51) Int. Cl.
*H04W 48/04* (2009.01)
*H04W 48/08* (2009.01)
*H04W 76/38* (2018.01)

(52) U.S. Cl.
CPC .......... *H04W 48/04* (2013.01); *H04W 48/08* (2013.01); *H04W 76/38* (2018.02)

(58) Field of Classification Search
CPC ...... H04W 48/04; H04W 48/08; H04W 76/38
(Continued)

(56) References Cited

U.S. PATENT DOCUMENTS

| 2017/0238221 | A1* | 8/2017 | Santhanam | H04W 36/08 370/331 |
| 2020/0396000 | A1* | 12/2020 | Ryu | H04W 24/02 |
| 2021/0243619 | A1* | 8/2021 | Watfa | H04W 48/06 |

FOREIGN PATENT DOCUMENTS

WO    2018174995 A1    9/2018

OTHER PUBLICATIONS

"3rd Generation Partnership Project, Technical Specification Group Gore Network and Terminals, Non-Access-Stratum (NAS) Protocol for Evolved Packet System (EPS); Stage 3 (Release 16)",3GPP Standard; Technical Specification, 3GPP TS 24.301, 3rd Generation Partnership Project (3GPP), Mobile Competence Centre, 650, Route Des Lucioles, F-06921, Sophia-Antipolis Cedex, France, vol. CT WG1, No. V16.4.0, Mar. 27, 2020 (Mar. 27, 2020), pp. 1-573, XP051861102, Retrieved from the Internet: URL: http://ftp.3gpp.org/Specs/archive/24_series/24.301/24301-g40.zip.

(Continued)

*Primary Examiner* — Faisal Choudhury
(74) *Attorney, Agent, or Firm* — Arent Fox, LLP

(57) ABSTRACT

The present disclosure relates to a user equipment (UE) dynamically adjusting a non-access stratum (NAS) timer. Specifically, the UE may determine operation in a wideband and support of an extended coverage (EC) restriction. The UE may further identify a duration of a non-access stratum (NAS) timer based on determining operation in the wideband and the EC restriction. The UE may further transmit an access request message to a network entity to trigger a mobility management procedure. The UE may further receive an acceptance message from the network entity indicating an unrestricted or restricted status of the EC restriction. The UE may further apply the duration to the NAS timer based on the acceptance message indicating the unrestricted or restricted status of the EC restriction received (Continued)

FIG. 1 from the network entity or a history of EC restrictions of a public land mobile network (PLMN) in a defined geographic area.

30 Claims, 7 Drawing Sheets

(58) Field of Classification Search
 USPC .......................................................... 370/328
 See application file for complete search history.

(56) References Cited

OTHER PUBLICATIONS

"3rd Generation Partnership Project, Technical specification Group Services and System Aspects; General Packet Radio Service (GPRS) enhancements for Evolved Universal Terrestrial Radio Access Network(E-UTRAN) access (Release 16)", 3GPP Standard, Technical Specification, 3GPP TS 23.401, 3rd Generation Partnership Project (3GPP), Mobile Competence Centre, 650, Route Des Lucioles, F-06921, Sophia-Antipolis Cedex, France, vol. SA WG2, No. V16.6.0, Mar. 27, 2020 (Mar. 27, 2020), pp. 1-436, XP051861088, Retrieved from the Internet: URL: http://.

Ericsson, et al., "5GS NAS Extended Timers for NB-N1 Mode and WB-N1/CE Mode Devices," 3GPP Draft, 3GPP TSG-CT WG1 Meeting #121, C1-198979, CP-193088, 3rd Generation Partnership Project (3GPP), Mobile Competence Centre, 650, Route Des Lucioles, F-06921, Sophia-Antipolis Cedex, France, vol. CT WG1, No. Reno (NV), USA, Nov. 11, 2019-Nov. 15, 2019, Dec. 2, 2019 (Dec. 2, 2019), XP051833489, 15 pages, Retrieved from the Internet: URL:https://ftp.3gpp.org/tsg_ct/TSG_CT/TSGC_86_Sitges/Docs/CP-193088.zip_24501_CR1647r2_(Rel-16).

International Search Report and Written Opinion—PCT/US2021/027789—ISA/EPO—dated Jun. 30, 2021.

* cited by examiner

US 11,540,203 B2

TECHNIQUES FOR USER EQUIPMENT (UE) DYNAMICALLY ADJUSTING A NON-ACCESS STRATUM (NAS) TIMER IN A WIRELESS COMMUNICATION SYSTEM

CROSS-REFERENCE RELATED APPLICATION(S)

This application claims the benefit of U.S. Provisional Patent Application No. 63/011,968, entitled "TECHNIQUES FOR USER EQUIPMENT (UE) DYNAMICALLY ADJUSTING A NON-ACCESS S 1RATUM (NAS) TIMER IN A WIRELESS COMMUNICATION SYSTEM" and filed on Apr. 17, 2020, which is expressly incorporated by reference herein in its entirety.

BACKGROUND

Aspects of the present disclosure relate generally to wireless communication systems, and more particularly, to a user equipment (UE) dynamically adjusting a non-access stratum (NAS) timer.

Wireless communication systems are widely deployed to provide various types of communication content such as voice, video, packet data, messaging, broadcast, and so on. These systems may be multiple-access systems capable of supporting communication with multiple users by sharing the available system resources (such as time, frequency, and power). Examples of such multiple-access systems include code-division multiple access (CDMA) systems, time-division multiple access (TDMA) systems, frequency-division multiple access (FDMA) systems, and orthogonal frequency-division multiple access (OFDMA) systems, and single-carrier frequency division multiple access (SC-FDMA) systems.

These multiple access technologies have been adopted in various telecommunication standards to provide a common protocol that enables different wireless devices to communicate on a municipal, national, regional, and even global level. For example, a fifth generation (5G) wireless communications technology (which can be referred to as NR) is envisaged to expand and support diverse usage scenarios and applications with respect to current mobile network generations. In some aspects, 5G communications technology can include: enhanced mobile broadband (eMBB) addressing human-centric use cases for access to multimedia content, services and data; ultra-reliable-low latency communications (URLLC) with certain specifications for latency and reliability; and massive machine type communications (mMTC), which can allow a very large number of connected devices and transmission of a relatively low volume of non-delay-sensitive information.

For example, for various communications technology such as, but not limited to NR, some implementations may increase transmission speed and flexibility but also transmission complexity. Thus, improvements in wireless communication operations may be desired.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

An example implementation includes a method of wireless communication at a user equipment (UE) including determining operation in a wideband and support of an extended coverage (EC) restriction. The method may further include identifying a duration of a non-access stratum (NAS) timer based on determining operation in the wideband and the EC restriction. The method may further include transmitting an access request message to a network entity to trigger a mobility management procedure. The method may further include receiving an acceptance message from the network entity indicating an unrestricted or restricted status of the EC restriction. The method may further include applying the duration to the NAS timer based on the acceptance message indicating the unrestricted or restricted status of the EC restriction received from the network entity, or a history of EC restrictions of a public land mobile network (PLMN) in a defined geographic area, and initiating the NAS timer according to the identified duration.

Another aspect of the subject matter described in this disclosure can be implemented in an apparatus for wireless communication. The apparatus may include memory including instructions and a processor in communication with the memory to execute the instructions to determine operation in a wideband and support of an EC restriction. The processor may further be configured to identify a duration of a NAS timer based on determining operation in the wideband and the EC restriction. The processor may further be configured to transmit an access request message to a network entity to trigger a mobility management procedure. The processor may further be configured to receive an acceptance message from the network entity indicating an unrestricted or restricted status of the EC restriction. The processor may further be configured to apply the duration to the NAS timer based on the acceptance message indicating the unrestricted or restricted status of the EC restriction received from the network entity, or a history of EC restrictions of a PLMN in a defined geographic area, and initiate the NAS timer according to the identified duration.

A further aspect of the subject matter described in this disclosure can be implemented in an apparatus for wireless communication. The apparatus may include means for determining operation in a wideband and support of an EC restriction. The apparatus further includes means for identifying a duration of a NAS timer based on determining operation in the wideband and the EC restriction. The apparatus may further include means for transmitting an access request message to a network entity to trigger a mobility management procedure. The apparatus may further include means for receiving an acceptance message from the network entity indicating an unrestricted or restricted status of the EC restriction. The apparatus may further include means for applying the duration to the NAS timer based on the acceptance message indicating the unrestricted or restricted status of the EC restriction received from the network entity, or a history of EC restrictions of a PLMN in a defined geographic area, and means for initiating the NAS timer according to the identified duration.

Another aspect of the subject matter described in this disclosure can be implemented in a non-transitory computer-readable medium including stored instructions of communications, executable by a processor to determine operation in a wideband and support of an EC restriction. The non-transitory computer-readable medium further including instructions to identify a duration of a NAS timer based on determining operation in the wideband and the EC restriction. The non-transitory computer-readable medium further including instructions to transmit an access request message to a network entity to trigger a mobility management procedure, receive an acceptance message from the network entity indicating an unrestricted or restricted status of the EC restriction. The non-transitory computer-readable medium further including instructions to apply the duration to the NAS timer based on the acceptance message indicating the unrestricted or restricted status of the EC restriction received from the network entity, or a history of EC restrictions of a PLMN in a defined geographic area. The non-transitory computer-readable medium further including instructions to initiate the NAS timer according to the identified duration.

To the accomplishment of the foregoing and related ends, the one or more aspects include the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

Like reference numbers and designations in the various drawings indicate like elements.

DETAILED DESCRIPTION

Figure 1:
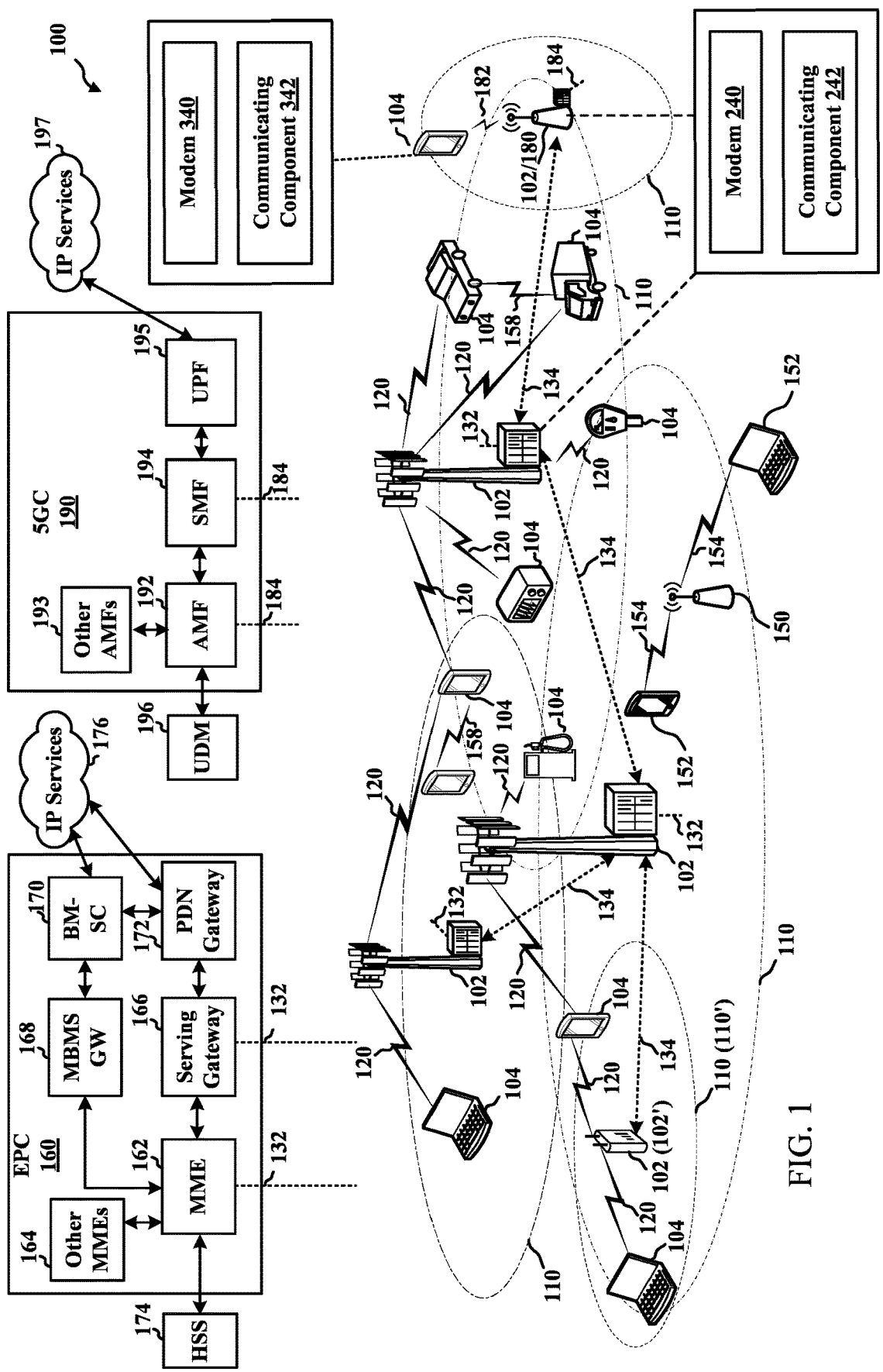
FIG. 1 illustrates an example of a wireless communication system.

Various aspects are now described with reference to the drawings. In the following description, for purposes of explanation, numerous specific details are set forth in order to provide a thorough understanding of one or more aspects. It may be evident, however, that such aspect(s) may be practiced without these specific details.

The described features generally relate to a user equipment (UE) dynamically adjusting a duration of a non-access stratum (NAS) timer. Specifically, a UE operating in category extended coverage (EC) can operate in at least two modes, e.g., either EC mode A or EC mode B. The coverage enhancement or EC may be achieved through transmission repetitions according to one of two defined modes—EC Mode A or EC Mode B. For example, in typical 4G operations, each transmission may span 1 millisecond, but in the EC modes each transmission may be repeated tens, hundreds or even thousands of times to improve the chances of successful transmission. EC mode A may be optimized for moderate coverage enhancement with no repetitious or a small number of repetitious transmissions, whereas EC mode B provides deeper coverage by permitting a large number of repetitious transmissions. An unrestricted EC operation would permit the UE to operating according to one of the EC Mode A or B. A restricted EC operation would not permit the UE to operate according to one or both of EC Mode A and/or B.

If a UE supports EC mode B, the UE may operate in a wideband (WB)-S1 mode, and the UE's usage setting may not be set to voice centric. The UE may apply an extended NAS timer value to cover slow network responses in these kind of deployments (i.e., WB-S1 or WB-N1). Examples of extended NAS timer durations at a UE include 'T3410' for sending an Attach request set to 85 seconds and 'T3430' for sending a tracking area update (TAU) request set to 77 seconds. Although the UE may support an EC mode B, the network may nonetheless determine to restrict the EC mode B to a number of UEs. For example, the UE may indicate support of a restricted use of EC by setting 'RestrictEC' to 'supported' in UE network capability information element (IE) of an Attach or TAU request message. The network may permit use of EC by transmitting an Attach or TAU accept message including a setting of 'RestrictEC' in an evolved packet system (EPS) network feature support IE. However, in some cases, the UE may trigger an initial access procedure without knowledge of whether access to an EC mode is permitted or restricted for a particular PLMN. The UE may typically use such information to set a duration of one or more NAS timers. Without such information, the UE may be unable to accurately set the duration the NAS timers, resulting in initial access failures.

As such, the present disclosure includes a method, apparatus, and non-statutory computer readable medium for wireless communications at a UE including determining operation in a wideband and support of an EC restriction, identifying a duration of a NAS timer based on determining operation in the wideband and the EC restriction, transmitting an access request message to a network entity to trigger a mobility management procedure, receiving an acceptance message from the network entity indicating an unrestricted or restricted status of the EC restriction, applying the duration to the NAS timer based on the acceptance message indicating the unrestricted or restricted status of the EC restriction received from the network entity, or a history of EC restrictions of a public land mobile network (PLMN) in a defined geographic area, and initiating the NAS timer according to the identified duration.

As used in this application, the terms "component," "module," "system" and the like are intended to include a computer-related entity, such as but not limited to hardware, software, a combination of hardware and software, or software in execution. For example, a component may be, but is not limited to being, a process running on a processor, a processor, an object, an executable, a thread of execution, a program, or a computer. By way of illustration, both an application running on a computing device and the computing device can be a component. One or more components can reside within a process or thread of execution and a component can be localized on one computer or distributed between two or more computers. In addition, these components can execute from various computer readable media having various data structures stored thereon. The components can communicate by way of local or remote processes such as in accordance with a signal having one or more data packets, such as data from one component interacting with another component in a local system, distributed system, or across a network such as the Internet with other systems by way of the signal. Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

Techniques described herein may be used for various wireless communication systems such as CDMA, TDMA, FDMA, OFDMA, SC-FDMA, and other systems. The terms "system" and "network" may often be used interchangeably. A CDMA system may implement a radio technology such as CDMA2000, Universal Terrestrial Radio Access (UTRA), etc. CDMA2000 covers IS-2000, IS-95, and IS-856 standards. IS-2000 Releases 0 and A are commonly referred to as CDMA2000 1x, 1X, etc. IS-856 (TIA-856) is commonly referred to as CDMA2000 1xEV-DO, High Rate Packet Data (HRPD), etc. UTRA includes Wideband CDMA (WCDMA) and other variants of CDMA. A TDMA system may implement a radio technology such as Global System for Mobile Communications (GSM). An OFDMA system may implement a radio technology such as Ultra Mobile Broadband (UMB), Evolved UTRA (E-UTRA), IEEE 802.11 (Wi-Fi), IEEE 802.16 (WiMAX), IEEE 802.20, Flash-OFDM™, etc. UTRA and E-UTRA are part of Universal Mobile Telecommunication System (UMTS). 3GPP Long Term Evolution (LTE) and LTE-Advanced (LTE-A) are new releases of UMTS that use E-UTRA. UTRA, E-UTRA, UMTS, LTE, LTE-A, and GSM are described in documents from an organization named "3rd Generation Partnership Project" (3GPP). CDMA2000 and UMB are described in documents from an organization named "3rd Generation Partnership Project 2" (3GPP2). The techniques described herein may be used for the systems and radio technologies mentioned above as well as other systems and radio technologies, including cellular (such as LTE) communications over a shared radio frequency spectrum band. The description below, however, describes an LTE/LTE-A system for purposes of example, and LTE terminology is used in much of the description below, although the techniques are applicable beyond LTE/LTE-A applications (such as to fifth generation (5G) NR networks or other next generation communication systems).

The following description provides examples, and is not limiting of the scope, applicability, or examples set forth in the claims. Changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in other examples.

Various aspects or features will be presented in terms of systems that can include a number of devices, components, modules, and the like. It is to be understood and appreciated that the various systems can include additional devices, components, modules, etc. or may not include all of the devices, components, modules etc. discussed in connection with the figures. A combination of these approaches also can be used.

FIG. 1 illustrates an example of a wireless communication system. The wireless communications system (also referred to as a wireless wide area network (WWAN)), includes an access network 100, base stations 102, UEs 104, an Evolved Packet Core (EPC) 160, or a 5G Core (5GC) 190. The base stations 102, which also may be referred to as network entities, may include macro cells (high power cellular base station) or small cells (low power cellular base station). The macro cells can include base stations. The small cells can include femtocells, picocells, and microcells. In an example, the base stations 102 also may include gNBs 180, as described further herein.

In one example, some nodes such as base station 102/gNB 180, may have a modem 240 and communicating component 242 for performing an initial access procedure with the UE 104 for access to a PLMN when the UE 104 is unaware of an EC mode restriction, as described herein. Though a base station 102/gNB 180 is shown as having the modem 240 and communicating component 242, this is one illustrative example, and substantially any node may include a modem 240 and communicating component 242 for providing corresponding functionalities described herein.

In another example, some nodes such as UE 104 of the wireless communication system may have a modem 340 and communicating component 342 for including determining an absence of information associated with an EC restriction for a PLMN of a current service coverage area, identifying a duration of a NAS timer based on determining the absence of the information associated with the EC restriction for the PLMN, transmitting an access request message to a network entity associated with the PLMN to trigger a mobility management procedure, and initiating the NAS timer according to the identified duration in response to transmitting the access request message to the network entity, as described herein. Though a UE 104 is shown as having the modem 340 and communicating component 342, this is one illustrative example, and substantially any node or type of node may include a modem 340 and communicating component 342 for providing corresponding functionalities described herein.

The base stations 102 configured for 4G LTE (which can collectively be referred to as Evolved Universal Mobile Telecommunications System (UMTS) Terrestrial Radio Access Network (E-UTRAN)) may interface with the EPC 160 through backhaul links 132 (such as using an S1 interface). The base stations 102 configured for 5G NR (which can collectively be referred to as Next Generation RAN (NG-RAN)) may interface with 5GC 190 through backhaul links 184. In addition to other functions, the base stations 102 may perform one or more of the following functions: transfer of user data, radio channel ciphering and deciphering, integrity protection, header compression, mobility control functions (such as handover, dual connectivity), inter-cell interference coordination, connection setup and release, load balancing, distribution for non-access stratum (NAS) messages, NAS node selection, synchronization, radio access network (RAN) sharing, multimedia broadcast multicast service (MBMS), subscriber and equipment trace, RAN information management (RIM), paging, positioning, and delivery of warning messages. The base stations 102 may communicate directly or indirectly (such as through the EPC 160 or 5GC 190) with each other over backhaul links 134 (such as using an X2 interface). The backhaul links 132, 134 or 184 may be wired or wireless.

The base stations 102 may wirelessly communicate with one or more UEs 104. Each of the base stations 102 may provide communication coverage for a respective geographic coverage area 110. There may be overlapping geographic coverage areas 110. For example, the small cell 102' may have a coverage area 110' that overlaps the coverage area 110 of one or more macro base stations 102. A network that includes both small cell and macro cells may be referred to as a heterogeneous network. A heterogeneous network also may include Home Evolved Node Bs (eNBs) (HeNBs), which may provide service to a restricted group, which can be referred to as a closed subscriber group (CSG). The communication links 120 between the base stations 102 and the UEs 104 may include uplink (UL) (also referred to as reverse link) transmissions from a UE 104 to a base station 102 or downlink (DL) (also referred to as forward link) transmissions from a base station 102 to a UE 104. The communication links 120 may use multiple-input and multiple-output (MIMO) antenna technology, including spatial multiplexing, beamforming, or transmit diversity. The communication links may be through one or more carriers. The base stations 102/UEs 104 may use spectrum up to Y MHz (such as 5, 10, 15, 20, 100, 400, etc. MHz) bandwidth per carrier allocated in a carrier aggregation of up to a total of Yx MHz (such as for x component carriers) used for transmission in the DL or the UL direction. The carriers may or may not be adjacent to each other. Allocation of carriers may be asymmetric with respect to DL and UL (such as more or less carriers may be allocated for DL than for UL). The component carriers may include a primary component carrier and one or more secondary component carriers. A primary component carrier may be referred to as a primary cell (PCell) and a secondary component carrier may be referred to as a secondary cell (SCell).

In another example, certain UEs 104 may communicate with each other using device-to-device (D2D) communication link 158. The D2D communication link 158 may use the DL/UL WWAN spectrum. The D2D communication link 158 may use one or more sidelink channels, such as a physical sidelink broadcast channel (PSBCH), a physical sidelink discovery channel (PSDCH), a physical sidelink shared channel (PSSCH), and a physical sidelink control channel (PSCCH). D2D communication may be through a variety of wireless D2D communications systems, such as for example, FlashLinQ, WiMedia, Bluetooth, ZigBee, Wi-Fi based on the IEEE 802.11 standard, LTE, or NR.

The wireless communications system may further include a Wi-Fi access point (AP) 150 in communication with Wi-Fi stations (STAs) 152 via communication links 154 in a 5 GHz unlicensed frequency spectrum. When communicating in an unlicensed frequency spectrum, the STAs 152/AP 150 may perform a clear channel assessment (CCA) prior to communicating in order to determine whether the channel is available.

The small cell 102' may operate in a licensed or an unlicensed frequency spectrum. When operating in an unlicensed frequency spectrum, the small cell 102' may employ NR and use the same 5 GHz unlicensed frequency spectrum as used by the Wi-Fi AP 150. The small cell 102', employing NR in an unlicensed frequency spectrum, may boost coverage to or increase capacity of the access network.

A base station 102, whether a small cell 102' or a large cell (such as macro base station), may include an eNB, gNodeB (gNB), or other type of base station. Some base stations, such as gNB 180 may operate in a traditional sub 6 GHz spectrum, in millimeter wave (mmW) frequencies, or near mmW frequencies in communication with the UE 104. When the gNB 180 operates in mmW or near mmW frequencies, the gNB 180 may be referred to as an mmW base station. Extremely high frequency (EHF) is part of the RF in the electromagnetic spectrum. EHF has a range of 30 GHz to 300 GHz and a wavelength between 1 millimeter and 10 millimeters. Radio waves in the band may be referred to as a millimeter wave. Near mmW may extend down to a frequency of 3 GHz with a wavelength of 100 millimeters. The super high frequency (SHF) band extends between 3 GHz and 30 GHz, also referred to as centimeter wave. Communications using the mmW/near mmW radio frequency band has extremely high path loss and a short range. The mmW base station, which may correspond to gNB 180, may utilize beamforming 182 with the UE 104 to compensate for the extremely high path loss and short range. A base station 102 referred to herein can include a gNB 180.

The EPC 160 may include a Mobility Management Entity (MME) 162, other MMEs 164, a Serving Gateway 166, a Multimedia Broadcast Multicast Service (MBMS) Gateway 168, a Broadcast Multicast Service Center (BM-SC) 170, and a Packet Data Network (PDN) Gateway 172. The MME 162 may be in communication with a Home Subscriber Server (HSS) 174. The MME 162 is the control node that processes the signaling between the UEs 104 and the EPC 160. Generally, the MME 162 provides bearer and connection management. All user Internet protocol (IP) packets are transferred through the Serving Gateway 166, which itself is connected to the PDN Gateway 172. The PDN Gateway 172 provides UE IP address allocation as well as other functions. The PDN Gateway 172 and the BM-SC 170 are connected to the IP Services 176. The IP Services 176 may include the Internet, an intranet, an IP Multimedia Subsystem (IMS), a PS Streaming Service, or other IP services. The BM-SC 170 may provide functions for MBMS user service provisioning and delivery. The BM-SC 170 may serve as an entry point for content provider MBMS transmission, may be used to authorize and initiate MBMS Bearer Services within a public land mobile network (PLMN), and may be used to schedule MBMS transmissions. The MBMS Gateway 168 may be used to distribute MBMS traffic to the base stations 102 belonging to a Multicast Broadcast Single Frequency Network (MBSFN) area broadcasting a particular service, and may be responsible for session management (start/stop) and for collecting eMBMS related charging information.

The 5GC 190 may include a Access and Mobility Management Function (AMF) 192, other AMFs 193, a Session Management Function (SMF) 194, and a User Plane Function (UPF) 195. The AMF 192 may be in communication with a Unified Data Management (UDM) 196. The AMF 192 can be a control node that processes the signaling between the UEs 104 and the 5GC 190. Generally, the AMF 192 can provide QoS flow and session management. User Internet protocol (IP) packets (such as from one or more UEs 104) can be transferred through the UPF 195. The UPF 195 can provide UE IP address allocation for one or more UEs, as well as other functions. The UPF 195 is connected to the IP Services 197. The IP Services 197 may include the Internet, an intranet, an IP Multimedia Subsystem (IMS), a PS Streaming Service, or other IP services.

The base station also may be referred to as a gNB, Node B, evolved Node B (eNB), an access point, a base transceiver station, a radio base station, a radio transceiver, a transceiver function, a basic service set (BSS), an extended service set (ESS), a transmit reception point (TRP), or some other suitable terminology. The base station 102 provides an access point to the EPC 160 or 5GC 190 for a UE 104. Examples of UEs 104 include a cellular phone, a smart phone, a session initiation protocol (SIP) phone, a laptop, a personal digital assistant (PDA), a satellite radio, a positioning system (such as satellite, terrestrial), a multimedia device, a video device, a digital audio player (such as MP3 player), a camera, a game console, a tablet, a smart device, robots, drones, an industrial/manufacturing device, a wearable device (such as a smart watch, smart clothing, smart glasses, virtual reality goggles, a smart wristband, smart jewelry (such as a smart ring, a smart bracelet)), a vehicle/a vehicular device, a meter (such as parking meter, electric meter, gas meter, water meter, flow meter), a gas pump, a large or small kitchen appliance, a medical/healthcare device, an implant, a sensor/actuator, a display, or any other similar functioning device. Some of the UEs 104 may be referred to as IoT devices (such as meters, pumps, monitors, cameras, industrial/manufacturing devices, appliances, vehicles, robots, drones, etc.). IoT UEs may include MTC/enhanced MTC (eMTC, also referred to as CAT-M, Cat M1) UEs, NB-IoT (also referred to as CAT NB1) UEs, as well as other types of UEs. In the present disclosure, eMTC and NB-IoT may refer to future technologies that may evolve from or may be based on these technologies. For example, eMTC may include FeMTC (further eMTC), eFeMTC (enhanced further eMTC), mMTC (massive MTC), etc., and NB-IoT may include eNB-IoT (enhanced NB-IoT), FeNB-IoT (further enhanced NB-IoT), etc. The UE 104 also may be referred to as a station, a mobile station, a subscriber station, a mobile unit, a subscriber unit, a wireless unit, a remote unit, a mobile device, a wireless device, a wireless communications device, a remote device, a mobile subscriber station, an access terminal, a mobile terminal, a wireless terminal, a remote terminal, a handset, a user agent, a mobile client, a client, or some other suitable terminology.

Figure 3:
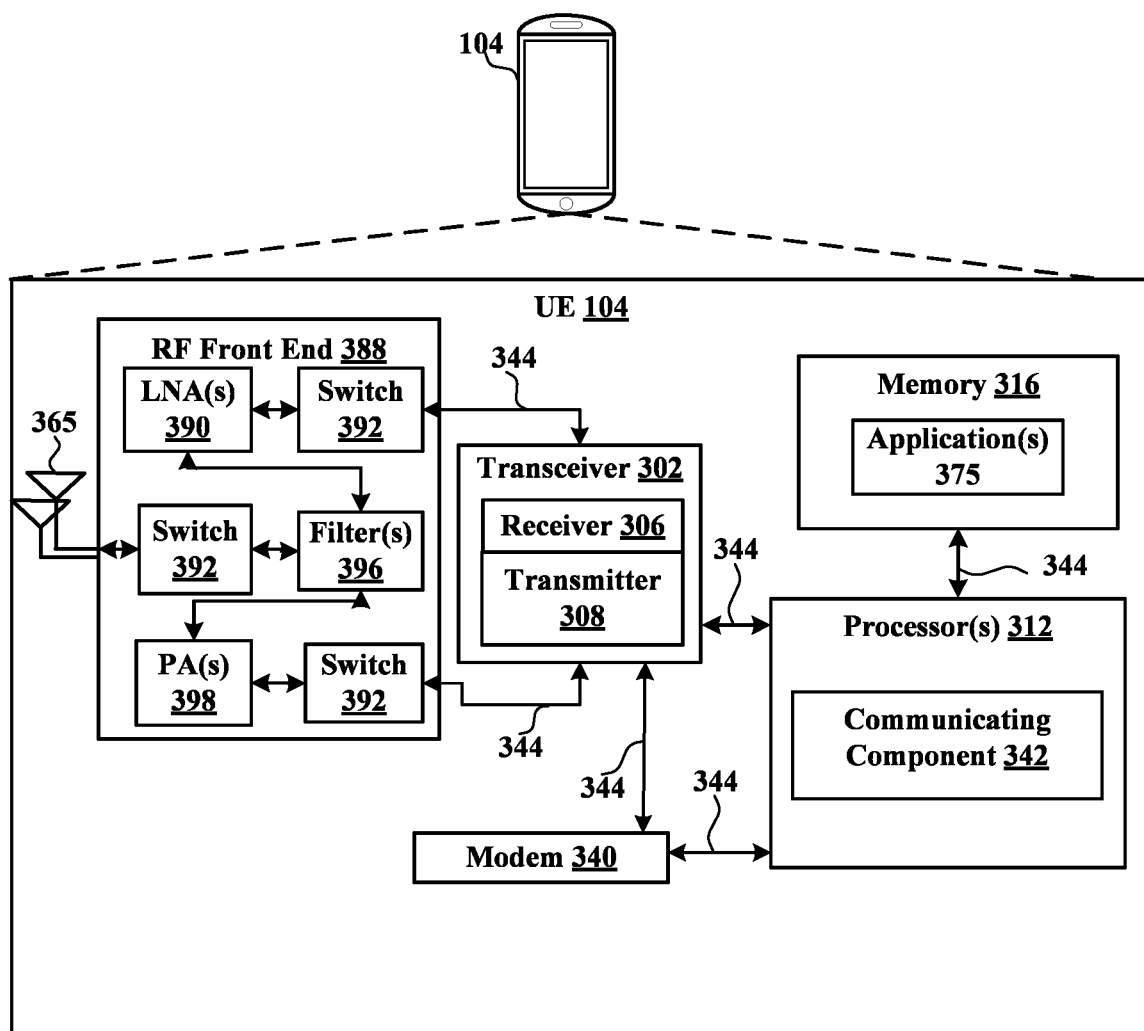
FIG. 3 is a block diagram illustrating an example of a user equipment (UE).
Figure 4:
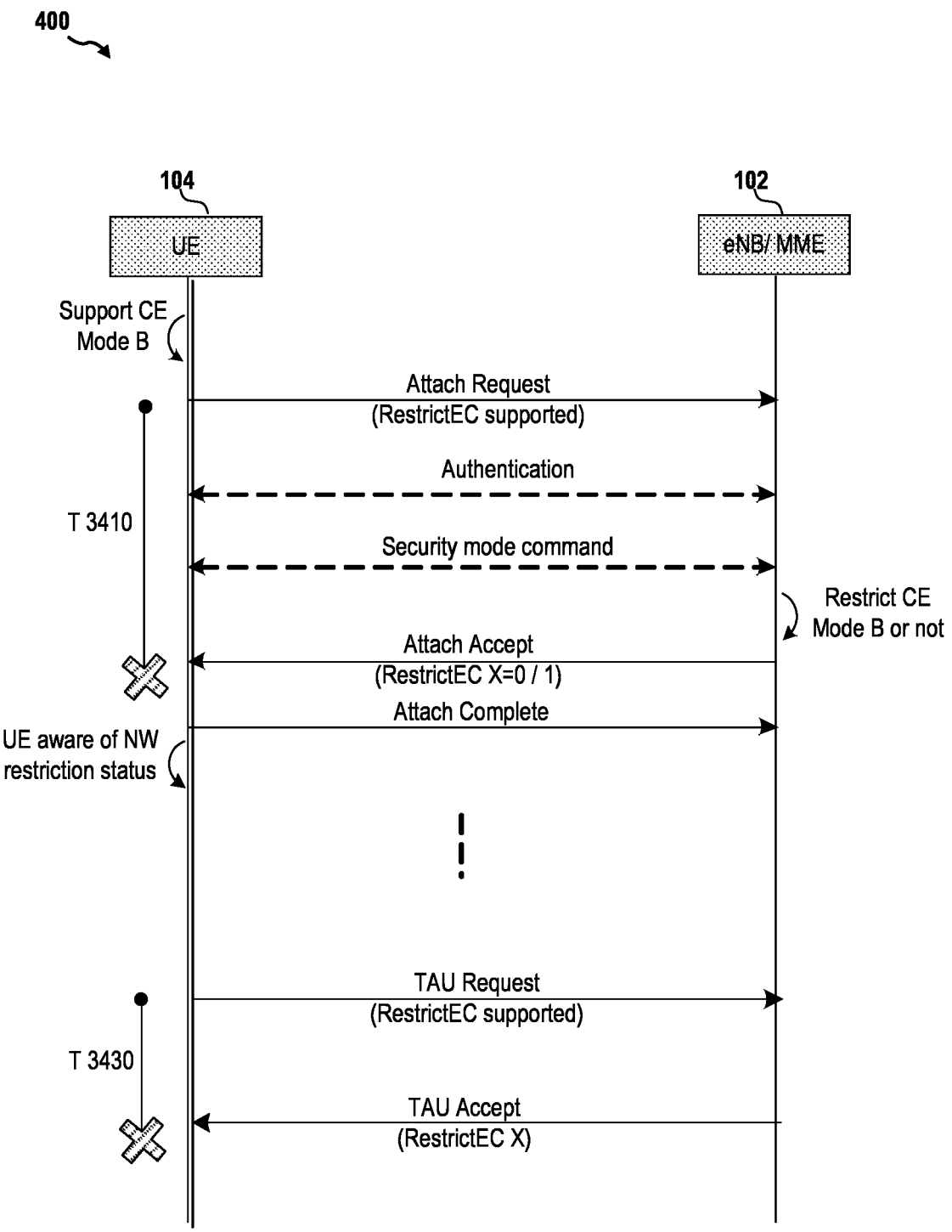
FIG. 4 is an example communication flow between a UE and a network entity (e.g., gNB) for an initial access attempt to a public land mobile network (PLMN).
Figure 5:
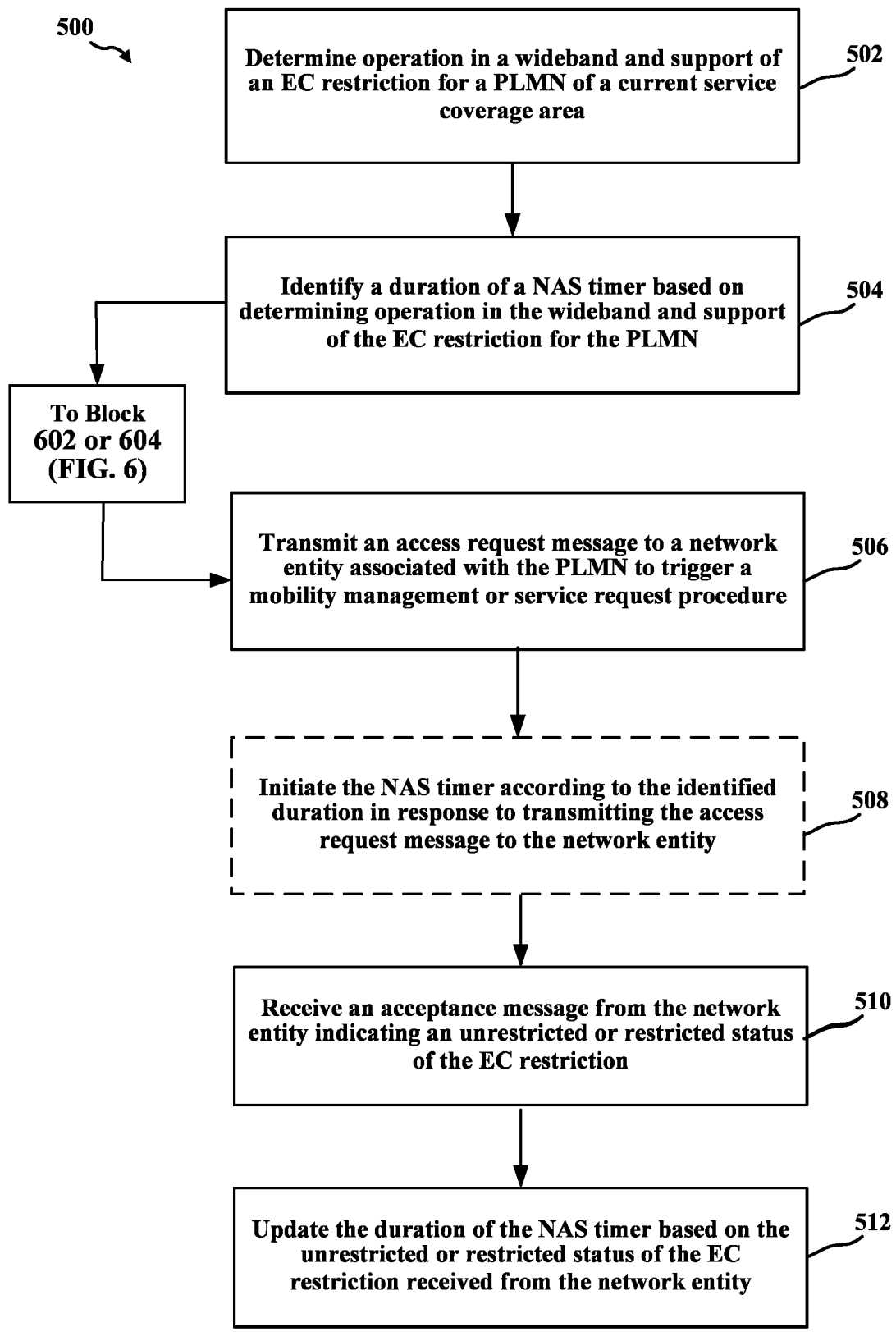
FIG. 5 is a flowchart of an example method of wireless communication at a UE.
Figure 6:
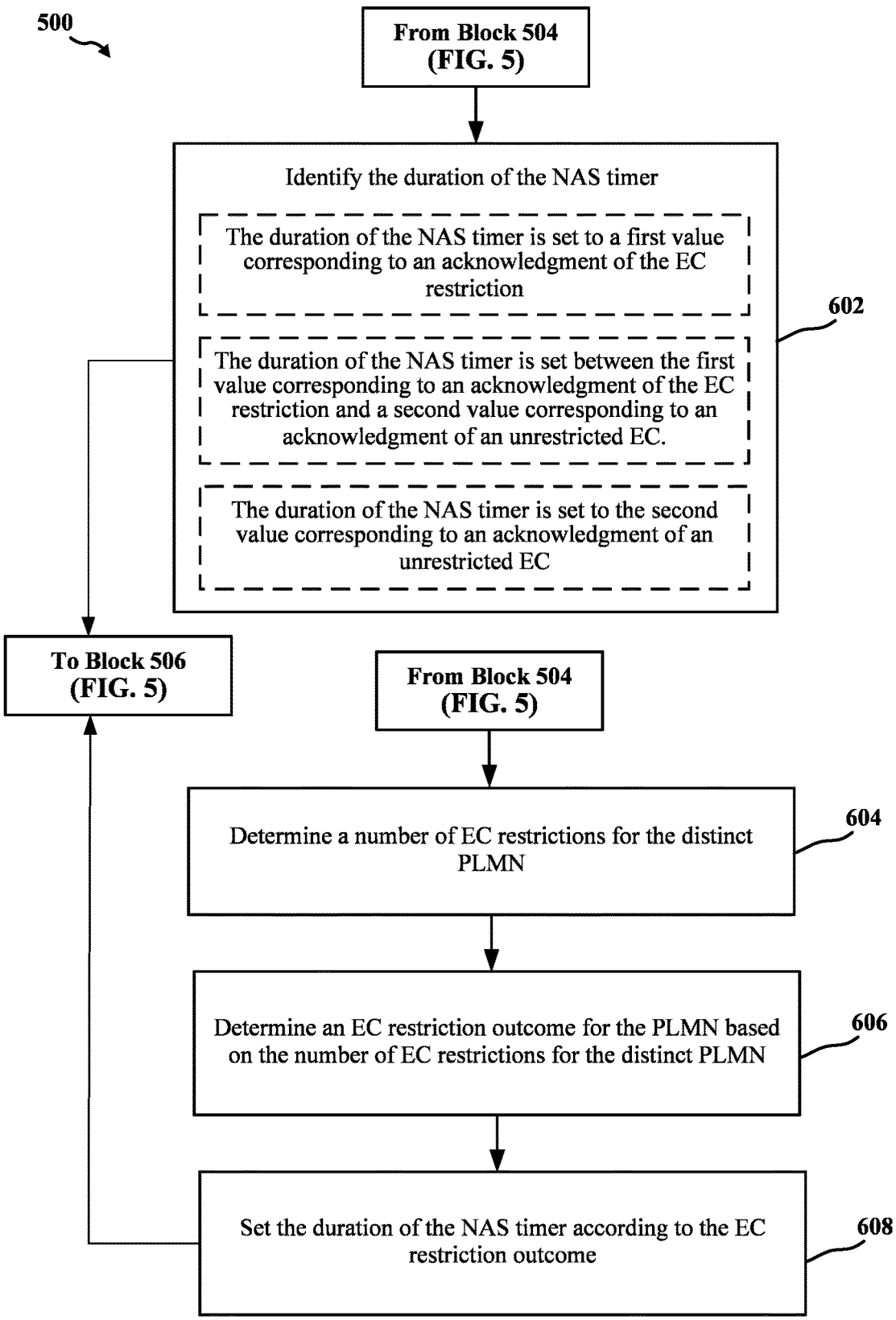
FIG. 6 is a flowchart of another example method of wireless communication at the UE.

Turning now to FIGS. 2-7, aspects are depicted with reference to one or more components and one or more methods that may perform the actions or operations described herein, where aspects in dashed line may be optional. Although the operations described below in FIGS. 5 and 6 are presented in a particular order or as being performed by an example component, it should be understood that the ordering of the actions and the components performing the actions may be varied, depending on the implementation. Moreover, it should be understood that the following actions, functions, or described components may be performed by a specially-programmed processor, a processor executing specially-programmed software or computer-readable media, or by any other combination of a hardware component or a software component capable of performing the described actions or functions.

Figure 2:
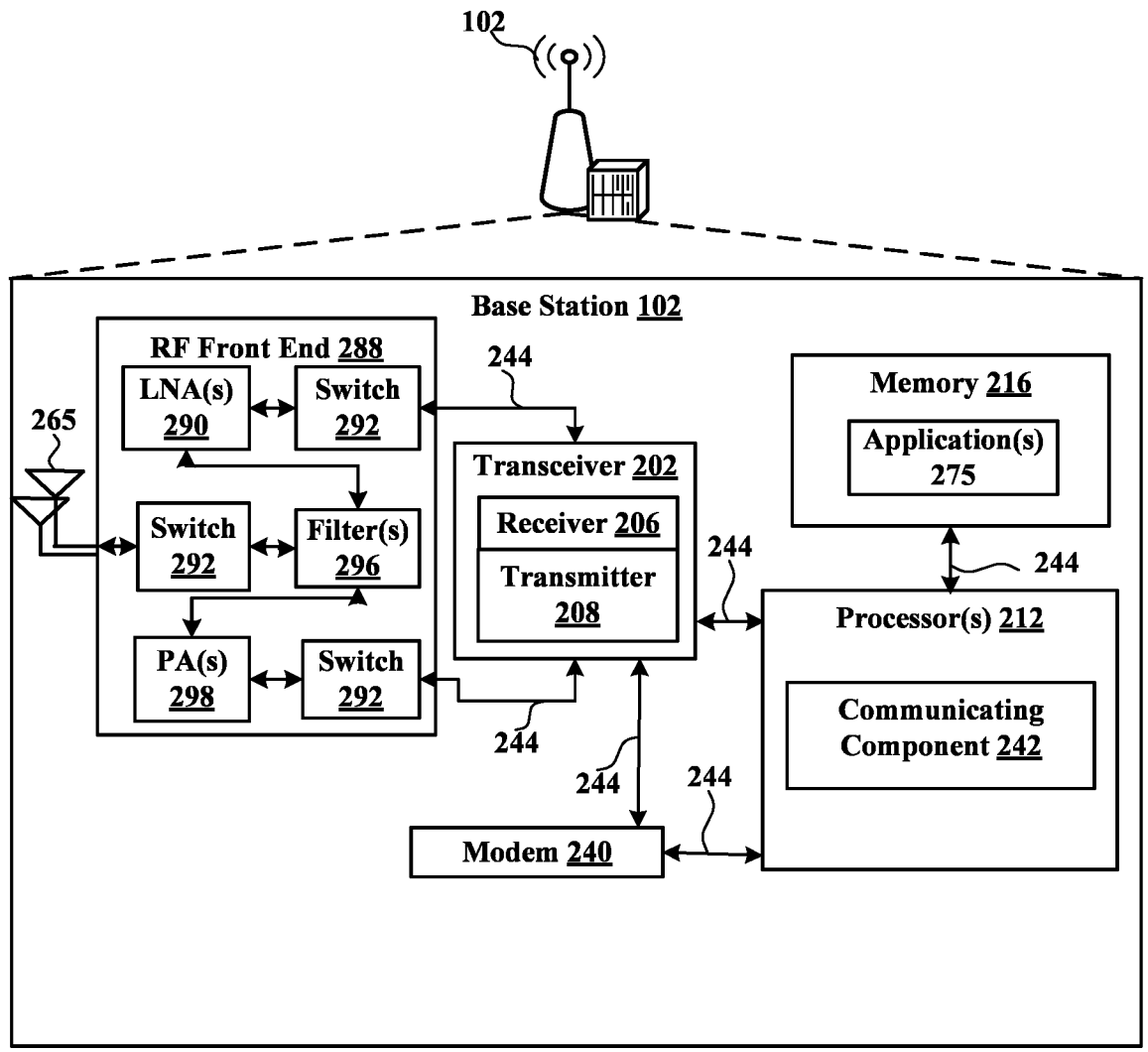
FIG. 2 is a block diagram illustrating an example of a network entity (also referred to as a base station).

FIG. 2 is a block diagram illustrating an example of a network entity (also referred to as a base station). The base station 102 (such as a base station 102 or gNB 180, as described above) may include a variety of components, some of which have already been described above and are described further herein, including components such as one or more processors 212 and memory 216 and transceiver 202 in communication via one or more buses 244, which may operate in conjunction with modem 240 or communicating component 242 for performing an initial access procedure with the UE 104 for access to a PLMN when the UE 104 is unaware of an EC mode restriction.

In some aspects, the one or more processors 212 can include a modem 240 or can be part of the modem 240 that uses one or more modem processors. Thus, the various functions related to communicating component 242 may be included in modem 240 or processors 212 and, in some aspects, can be executed by a single processor, while in other aspects, different ones of the functions may be executed by a combination of two or more different processors. For example, in some aspects, the one or more processors 212 may include any one or any combination of a modem processor, or a baseband processor, or a digital signal processor, or a transmit processor, or a receiver processor, or a transceiver processor associated with transceiver 202. In other aspects, some of the features of the one or more processors 212 or modem 240 associated with communicating component 242 may be performed by transceiver 202.

Also, memory 216 may be configured to store data used herein or local versions of applications 275 or communicating component 242 or one or more of its subcomponents being executed by at least one processor 212. Memory 216 can include any type of computer-readable medium usable by a computer or at least one processor 212, such as random access memory (RAM), read only memory (ROM), tapes, magnetic discs, optical discs, volatile memory, non-volatile memory, and any combination thereof. In some aspects, for example, memory 216 may be a non-transitory computer-readable storage medium that stores one or more computer-executable codes defining communicating component 242 or one or more of its subcomponents, or data associated therewith, when base station 102 is operating at least one processor 212 to execute communicating component 242 or one or more of its subcomponents.

Transceiver 202 may include at least one receiver 206 and at least one transmitter 208. Receiver 206 may include hardware or software executable by a processor for receiving data, the code including instructions and being stored in a memory (such as computer-readable medium). Receiver 206 may be, for example, a radio frequency (RF) receiver. In some aspects, receiver 206 may receive signals transmitted by at least one base station 102. Additionally, receiver 206 may process such received signals, and also may obtain measurements of the signals, such as, but not limited to, Ec/Io, signal-to-noise ratio (SNR), reference signal received power (RSRP), received signal strength indicator (RSSI), etc. Transmitter 208 may include hardware or software executable by a processor for transmitting data, the code including instructions and being stored in a memory (such as computer-readable medium). A suitable example of transmitter 208 may including, but is not limited to, an RF transmitter.

Moreover, in some aspects, base station 102 may include RF front end 288, which may operate in communication with one or more antennas 265 and transceiver 202 for receiving and transmitting radio transmissions, for example, wireless communications transmitted by at least one base station 102 or wireless transmissions transmitted by UE 104. RF front end 288 may be connected to one or more antennas 265 and can include one or more low-noise amplifiers (LNAs) 290, one or more switches 292, one or more power amplifiers (PAs) 298, and one or more filters 296 for transmitting and receiving RF signals. The antennas 265 may include one or more antennas, antenna elements, or antenna arrays.

In some aspects, LNA 290 can amplify a received signal at a desired output level. In some aspects, each LNA 290 may have a specified minimum and maximum gain values. In some aspects, RF front end 288 may use one or more switches 292 to select a particular LNA 290 and its specified gain value based on a desired gain value for a particular application.

Further, for example, one or more PA(s) 298 may be used by RF front end 288 to amplify a signal for an RF output at a desired output power level. In some aspects, each PA 298 may have specified minimum and maximum gain values. In some aspects, RF front end 288 may use one or more switches 292 to select a particular PA 298 and its specified gain value based on a desired gain value for a particular application.

Also, for example, one or more filters 296 can be used by RF front end 288 to filter a received signal to obtain an input RF signal. Similarly, in some aspects, for example, a respective filter 296 can be used to filter an output from a respective PA 298 to produce an output signal for transmission. In some aspects, each filter 296 can be connected to a specific LNA 290 or PA 298. In some aspects, RF front end 288 can use one or more switches 292 to select a transmit or receive path using a specified filter 296, LNA 290, or PA 298, based on a configuration as specified by transceiver 202 or processor 212.

As such, transceiver 202 may be configured to transmit and receive wireless signals through one or more antennas 265 via RF front end 288. In some aspects, transceiver may be tuned to operate at specified frequencies such that UE 104 can communicate with, for example, one or more base stations 102 or one or more cells associated with one or more base stations 102. In some aspects, for example, modem 240 can configure transceiver 202 to operate at a specified frequency and power level based on the UE configuration of the UE 104 and the communication protocol used by modem 240.

In some aspects, modem 240 can be a multiband-multimode modem, which can process digital data and communicate with transceiver 202 such that the digital data is sent and received using transceiver 202. In some aspects, modem 240 can be multiband and be configured to support multiple frequency bands for a specific communications protocol. In some aspects, modem 240 can be multimode and be configured to support multiple operating networks and communications protocols. In some aspects, modem 240 can control one or more components of UE 104 (such as RF front end 288, transceiver 202) to enable transmission or reception of signals from the network based on a specified modem configuration. In some aspects, the modem configuration can be based on the mode of the modem and the frequency band in use. In another aspect, the modem configuration can be based on UE configuration information associated with UE 104 as provided by the network during cell selection or cell reselection.

In some aspects, the processor(s) 212 may correspond to one or more of the processors described in connection with the UE in FIGS. 4 and 6. Similarly, the memory 216 may correspond to the memory described in connection with the UE in FIG. 7.

FIG. 3 is a block diagram illustrating an example of a UE 104. The UE 104 may include a variety of components, some of which have already been described above and are described further herein, including components such as one or more processors 312 and memory 316 and transceiver 302 in communication via one or more buses 344, which may operate in conjunction with modem 340 or communicating component 342 configured to perform an initial access procedure for access to a PLMN without knowledge of an EC mode restriction.

The transceiver 302, receiver 306, transmitter 308, one or more processors 312, memory 316, applications 375, buses 344, RF front end 388, LNAs 390, switches 392, filters 396, PAs 398, and one or more antennas 365 may be the same as or similar to the corresponding components of base station 102, as described above, but configured or otherwise programmed for base station operations as opposed to base station operations.

In some aspects, the processor(s) 312 may correspond to one or more of the processors described in connection with the base station in FIG. 7. Similarly, the memory 316 may correspond to the memory described in connection with the base station in FIG. 7.

FIG. 4 is an example communication flow between a UE and a network entity (e.g., eNB or gNB) for an initial access attempt to a PLMN. For an initial access attempt to a PLMN, a UE 104 may trigger an Attach procedure or a TAU procedure depending on an EPS mobility management (EMM) status by sending an attach request message to the gNB 102, without knowing whether EC mode B is permitted or restricted in the PLMN. For initial access attempt to the PLMN when the UE 104 not aware of PLMN restriction, the UE may set NAS timers to a restricted value (e.g., 15 sec) or an unrestricted value (85 sec). As shown in FIG. 4, the UE may determine a timer duration value for T3410 in the event the UE does not receive any sort of indication as to an EC mode B restriction for the PLMN. Further, if the network triggers other procedures (e.g. authentication), the UE may determine timer duration values for corresponding NAS timers as well. In some implementations, the network may indicate the status of an EC Mode B restriction. In such case, the UE may set the NAS timers accordingly. For example, as shown in T3430, UE sets the NAS timer during T3430 based on network feedback.

In some implementations, the UE may set the NAS timer to any one of a number of duration values when the UE is not aware of an EC mode B restriction for the PLMN. In a first implementation, with absence of any knowledge about the PLMN restricting EC Mode B, the UE may set the NAS timer to a restrictive value (e.g., 5-15 sec). The resulting consequence may be if the PLMN is not restricting the EC Mode B for a UE, completing an initial NAS procedure may take a longer because of an inherited delay in the EC Mode B access, which in turn may affect completing the NAS procedure.

In a second implementation, the UE may set the NAS timer to a timer value between a restrictive value (e.g., 5-15 sec) and an unrestricted value (e.g., 85 sec) based on no knowledge of an EC Mode B restriction by the PLMN. In a third implementation, with absence of any knowledge about the PLMN restricting EC Mode B, the UE may set a NAS timer to an unrestricted value (e.g., 85 sec). By doing so, however, if PLMN is restricting EC Mode B for a UE, in some cases the UE may be waiting for a network response longer than usual. In a fourth implementation, the UE may store or maintain a history of the PLMN or other PLMNs' behavior regarding EC Mode B restriction for the UE in a same country (or geographical region or MCC). The UE may use the historical data to predict a probable outcome for new PLMN and set the NAS timer accordingly.

During an initial access attempt using an Attach or TAU procedure, the network may trigger an authentication procedure such that a number of NAS timers may be configured as described herein: T3416 for storing RAND/RES: UE set duration of 48 sec (vs. original of 30 sec set by network), T3418 for authentication failure (MAC): UE set duration of 38 sec (vs. original of 20 sec set by network), and/or T3420 for authentication failure (Synchronization): UE set duration of 33 sec (vs. original of 15 sec set by network).

FIG. 5 is a flowchart of an example method 500 of wireless communication at an apparatus of a UE. In an example, a UE 104 can perform the functions described in method 500 using one or more of the components described in FIGS. 1, 3 and 7.

At block 502, the method 500 may determine operation in a wideband and support of an EC restriction for a PLMN of a current service coverage area. In some aspects, the communicating component 342, such as in conjunction with processor(s) 312, memory 316, or transceiver 302, may be configured to determine operation in a wideband and support of an EC restriction for a PLMN of a current service coverage area. Thus, the UE 104, the processor(s) 312, the communicating component 342 or one of its subcomponents may define the means for determining operation in a wideband and support of an EC restriction for a PLMN of a current service coverage area. For example, the processor 312 of the UE 104 may, in conjunction with one or more applications 375 residing at the memory 316, may determine, based on UE configuration, operation in a wideband (i.e., WB-N1) and support of an EC restriction (i.e., CE mode B).

In some implementations, the EC restriction may correspond to an EC Mode B restriction.

At block 504, the method 500 may identify a duration of a NAS timer based on determining operation in the wideband and support of the EC restriction for the PLMN. In some aspects, the communicating component 342, such as in conjunction with processor(s) 312, memory 316, or transceiver 302, may be configured to identify a duration of a NAS timer based on determining operation in the wideband and support of the EC restriction for the PLMN. Thus, the UE 104, the processor(s) 312, the communicating component 342 or one of its subcomponents may define the means for identifying a duration of a NAS timer based on determining operation in the wideband and support of the EC restriction for the PLMN. For example, using information relating to the wideband operation and the EC restriction, the processor 312 of the UE 104 may, in conjunction with one or more applications 375 residing at the memory 316, may identify a duration of a NAS timer In some implementations, the method 500 apply an initial duration of the NAS timer corresponding to a configured length of time set by the UE without an indication from the network entity of the EC restriction prior to receiving the acceptance message from the network entity, and where the initial duration is smaller than the identified duration. In some aspects, the communicating component 342, such as in conjunction with processor(s) 312, memory 316, or transceiver 302, may be configured to apply an initial duration of the NAS timer corresponding to a configured length of time set by the UE without an indication from the network entity of the EC restriction prior to receiving the acceptance message from the network entity, and where the initial duration is smaller than the identified duration. Thus, the UE 104, the processor(s) 312, the communicating component 342 or one of its subcomponents may define the means for applying an initial duration of the NAS timer corresponding to a configured length of time set by the UE without an indication from the network entity of the EC restriction prior to receiving the acceptance message from the network entity, and where the initial duration is smaller than the identified duration.

At block 506, the method 500 may transmit an access request message to a network entity associated with the PLMN to trigger a mobility management procedure or service request procedure. In some aspects, the communicating component 342, such as in conjunction with processor(s) 312, memory 316, or transceiver 302, may be configured to transmit an access request message to a network entity associated with the PLMN to trigger a mobility management procedure or service request procedure. Thus, the UE 104, the processor(s) 312, the communicating component 342 or one of its subcomponents may define the means for transmitting an access request message to a network entity associated with the PLMN to trigger a mobility management procedure or service request procedure. For example, the processor 312 of the UE 104 may activate the transceiver 302 and associated RF front end 388 components to transmit an access request message to a network entity associated with the PLMN to trigger a mobility management procedure or service request procedure.

In some implementations, the access request message may correspond to one of an attached request message, an authentication response message, an authentication failure message, a TAU request message, a registration for mobility message, an initial registration request or service request message.

At block 508, the method 500 may initiate the NAS timer according to the identified duration in response to transmitting the access request message to the network entity. In some aspects, the communicating component 342, such as in conjunction with processor(s) 312, memory 316, or transceiver 302, may be configured to initiate the NAS timer according to the identified duration in response to transmitting the access request message to the network entity. Thus, the UE 104, the processor(s) 312, the communicating component 342 or one of its subcomponents may define the means for initiating the NAS timer according to the identified duration in response to transmitting the access request message to the network entity. For example, using the identified duration, the processor 312 of the UE 104 may, in conjunction with one or more applications 375 residing at the memory 316, may initiate the NAS timer.

At block 510, the method 500 may receive an acceptance message from the network entity indicating an unrestricted or restricted status of the EC restriction during the mobility management procedure. In some aspects, the communicating component 342, such as in conjunction with processor(s) 312, memory 316, or transceiver 302, may be configured to receive an acceptance message from the network entity indicating an unrestricted or restricted status of the EC restriction. Thus, the UE 104, the processor(s) 312, the communicating component 342 or one of its subcomponents may define the means for receiving an acceptance message from the network entity indicating an unrestricted or restricted status of the EC restriction. For example, the processor 312 of the UE 104 may activate the transceiver 302 and associated RF front end 388 components to receive an acceptance message from the network entity indicating an unrestricted or restricted status of the EC restriction during the mobility management procedure.

In some aspects, the unrestricted status may indicate that the use of enhanced coverage is not restricted, or CE mode B is not restricted.

At block 512, the method 500 may update the duration of the NAS timer based on the unrestricted or restricted status of the EC restriction received from the network entity. In some aspects, the communicating component 342, such as in conjunction with processor(s) 312, memory 316, or transceiver 302, may be configured to update or apply the duration of the NAS timer based on the unrestricted or restricted status of the EC restriction received from the network entity. Thus, the UE 104, the processor(s) 312, the communicating component 342 or one of its subcomponents may define the means for updating the duration of the NAS timer based on the unrestricted or restricted status of the EC restriction received from the network entity. For example, the processor 312 of the UE 104 may, in conjunction with one or more applications 375 residing at the memory 316, may update the duration of the NAS timer based on the unrestricted or restricted status of the EC restriction received from the network entity, or a history of EC restrictions of a public land mobile network (PLMN) in a defined geographic area.

FIG. 6 is a flowchart of further example implementations for wireless communication in conjunction with FIG. 5. In an example, a UE 104 can perform the functions described in method 500 using one or more of the components described in FIGS. 1, 3 and 7.

At block 602, to identify the duration of the NAS timer for the mobility management procedure, the method 500 may set the duration of the NAS timer to a first value corresponding to an indication or acknowledgment of the EC restriction, i.e., restriction on the use of EC (e.g., 15 seconds), to a distinct value between a second value corresponding to an indication of the EC restriction and a third value (e.g., 85 seconds) corresponding to an indication of an unrestricted EC, or the third value corresponding to an indication or acknowledgment of an unrestricted EC. For service request procedure, NAS timer is set to duration based on previous knowledge of the EC restriction on current serving PLMN.

In some aspects, the communicating component 342, such as in conjunction with processor(s) 312, memory 316, or transceiver 302, may be configured to identify the duration of the NAS timer, the method 500 may set the duration of the NAS timer to a first value corresponding to an indication of the EC restriction (e.g., 15 seconds), to a distinct value between a second value corresponding to an indication of the EC restriction and a third value (e.g., 85 seconds) corresponding to an indication of an unrestricted EC, or the third value corresponding to an indication of an unrestricted EC.

Thus, the UE 104, the processor(s) 312, the communicating component 342 or one of its subcomponents may define the means for identifying the duration of the NAS timer, the method 500 may set the duration of the NAS timer to a first value corresponding to an indication of the EC restriction (e.g., 15 seconds), to a distinct value between a second value corresponding to an indication of the EC restriction and a third value (e.g., 85 seconds) corresponding to an indication of an unrestricted EC, or the third value corresponding to an indication of an unrestricted EC.

Implementations of block 604 to 608 relate to when the duration of the NAS timer is based on past EC restrictions of the PLMN and/or a distinct PLMN in a defined geographic area, and the defined geographic area including the PLMN and distinct PLMN. For example, the PLMN and the different PLMN may be part of or provide coverage within a similar country.

At block 604, the method 500 may determine a number of EC restrictions for the distinct PLMN. In some aspects, the communicating component 342, such as in conjunction with processor(s) 312, memory 316, or transceiver 302, may be configured to determine a number of EC restrictions for the distinct PLMN. Thus, the UE 104, the processor(s) 312, the communicating component 342 or one of its subcomponents may define the means for determining a number of EC restrictions for the distinct PLMN. For example, the number of EC restrictions may be a count of EC restrictions applied by the PLMN or the distinct PLMN to the UE with respect to operating in an EC Mode B. The count may also be representative of a percentage or probability of EC restriction based on or a function of a total previous number of EC restrictions and a total number of initial access attempts for a given PLMN.

At block 606, the method 500 may determine an EC restriction outcome for the PLMN based on the number of EC restrictions for the distinct PLMN. In some aspects, the communicating component 342, such as in conjunction with processor(s) 312, memory 316, or transceiver 302, may be configured to determine an EC restriction outcome for the PLMN based on the number of EC restrictions for the distinct PLMN. Thus, the UE 104, the processor(s) 312, the communicating component 342 or one of its subcomponents may define the means for determining an EC restriction outcome for the PLMN based on the number of EC restrictions for the distinct PLMN.

In some implementations, the EC restriction outcome may correspond to a likelihood of EC restriction by the PLMN based on past EC restrictions of the distinct PLMN sharing the geographic area.

At block 608, the method 500 may set the duration of the NAS timer according to the EC restriction outcome. In some aspects, the communicating component 342, such as in conjunction with processor(s) 312, memory 316, or transceiver 302, may be configured to set the duration of the NAS timer according to the EC restriction outcome. Thus, the UE 104, the processor(s) 312, the communicating component 342 or one of its subcomponents may define the means for setting the duration of the NAS timer according to the EC restriction outcome.

Figure 7:
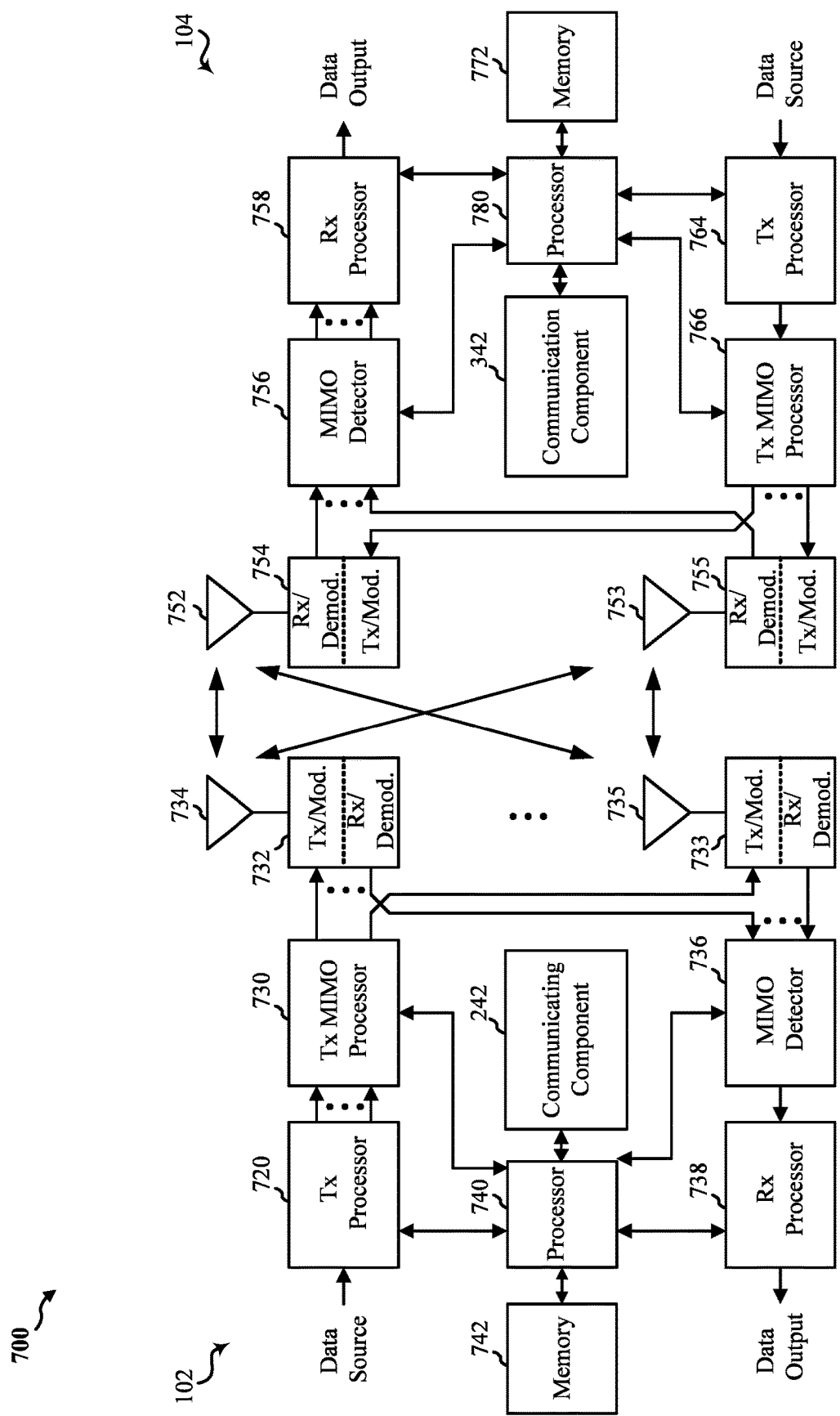
FIG. 7 is a block diagram illustrating an example of a multiple-input multiple-output (MIMO) communication system including a base station and a UE.

FIG. 7 is a block diagram of a MIMO communication system 700 including a base station 102 and a UE 104. The MIMO communication system 700 may be configured to implement the NAS timer configuration techniques described herein. The MIMO communication system 700 may illustrate aspects of the wireless communication access network 100 described with reference to FIG. 1. The base station 102 may be an example of aspects of the base station 102 described with reference to FIG. 1. The base station 102 may be equipped with antennas 734 and 735, and the UE 104 may be equipped with antennas 752 and 753. In the MIMO communication system 700, the base station 102 may be able to send data over multiple communication links at the same time. Each communication link may be called a "layer" and the "rank" of the communication link may indicate the number of layers used for communication. For example, in a 2×2 MIMO communication system where base station 102 transmits two "layers," the rank of the communication link between the base station 102 and the UE 104 is two.

At the base station 102, a transmit (Tx) processor 720 may receive data from a data source. The transmit processor 720 may process the data. The transmit processor 720 also may generate control symbols or reference symbols. A transmit MIMO processor 730 may perform spatial processing (such as precoding) on data symbols, control symbols, or reference symbols, if applicable, and may provide output symbol streams to the transmit modulator/demodulators 732 and 733. Each modulator/demodulator 732 through 733 may process a respective output symbol stream (such as for OFDM, etc.) to obtain an output sample stream. Each modulator/demodulator 732 through 733 may further process (such as convert to analog, amplify, filter, and upconvert) the output sample stream to obtain a DL signal. In one example, DL signals from modulator/demodulators 732 and 733 may be transmitted via the antennas 734 and 735, respectively.

The UE 104 may be an example of aspects of the UEs 104 described with reference to FIGS. 1 and 2. At the UE 104, the UE antennas 752 and 753 may receive the DL signals from the base station 102 and may provide the received signals to the modulator/demodulators 754 and 755, respectively. Each modulator/demodulator 754 through 755 may condition (such as filter, amplify, downconvert, and digitize) a respective received signal to obtain input samples. Each modulator/demodulator 754 through 755 may further process the input samples (such as for OFDM, etc.) to obtain received symbols. A MIMO detector 756 may obtain received symbols from the modulator/demodulators 754 and 755, perform MIMO detection on the received symbols, if applicable, and provide detected symbols. A receive (Rx) processor 758 may process (such as demodulate, deinterleave, and decode) the detected symbols, providing decoded data for the UE 104 to a data output, and provide decoded control information to a processor 780, or memory 782.

The processor 780 may in some cases execute stored instructions to instantiate a communicating component 242 (see such as FIGS. 1 and 2). The processor 740 may in some cases execute stored instructions to instantiate a communicating component 342 (see such as FIGS. 1 and 3).

On the uplink (UL), at the UE 104, a transmit processor 764 may receive and process data from a data source. The transmit processor 764 also may generate reference symbols for a reference signal. The symbols from the transmit processor 764 may be precoded by a transmit MIMO processor 766 if applicable, further processed by the modulator/demodulators 754 and 755 (such as for SC-FDMA, etc.), and be transmitted to the base station 102 in accordance with the communication parameters received from the base station 102. At the base station 102, the UL signals from the UE 104 may be received by the antennas 734 and 735, processed by the modulator/demodulators 732 and 733, detected by a MIMO detector 736 if applicable, and further processed by a receive processor 738. The receive processor 738 may provide decoded data to a data output and to the processor 740 or memory 742.

The components of the UE 104 may, individually or collectively, be implemented with one or more ASICs adapted to perform some or all of the applicable functions in hardware. Each of the noted modules may be a means for performing one or more functions related to operation of the MIMO communication system 700. Similarly, the components of the base station 102 may, individually or collectively, be implemented with one or more ASICs adapted to perform some or all of the applicable functions in hardware. Each of the noted components may be a means for performing one or more functions related to operation of the MIMO communication system 700.

Some Additional Examples

The aspects described herein additionally include one or more of the following aspect examples described in the following numbered clauses.

1. A method of wireless communication at a user equipment (UE), comprising:
   determining operation in a wideband and support of an extended coverage (EC) restriction;
   identifying a duration of a non-access stratum (NAS) timer based on determining the operation in the wideband and the EC restriction;
   transmitting an access request message to a network entity to trigger a mobility management procedure;
   receiving an acceptance message from the network entity indicating an unrestricted or restricted status of the EC restriction;
   applying the duration to the NAS timer based on the acceptance message indicating the unrestricted or restricted status of the EC restriction received from the network entity or a history of EC restrictions of a public land mobile network (PLMN) in a defined geographic area; and
   initiating the NAS timer according to the identified duration.

2. The method of clause 1, further comprising applying an initial duration of the NAS timer corresponding to a configured length of time set by the UE without an indication from the network entity of the EC restriction prior to receiving the acceptance message from the network entity, and wherein the initial duration is smaller than the identified duration.

3. The method of any preceding clause, wherein the EC restriction corresponds to an EC Mode B restriction.

4. The method of any preceding clause, wherein the duration of the NAS timer is set to a value corresponding to an indication of the EC restriction.

5. The method of any preceding clause, wherein the duration of the NAS timer corresponds to a timer value between 5 and 15 seconds.

6. The method of any preceding clause, wherein the duration of the NAS timer is set between a value corresponding to an indication of the EC restriction and a value corresponding to an indication of an unrestricted EC.

7. The method of any preceding clause, wherein the duration of the NAS timer corresponds to a timer value between 15 seconds and 85 seconds.

8. The method of any preceding clause, wherein the duration of the NAS timer is set to a value corresponding to an indication of an unrestricted EC.

9. The method of any preceding clause, wherein the duration of the NAS timer corresponds to 85 seconds.

10. The method of any preceding clause, wherein the duration of the NAS timer is based on past EC restrictions of a public land mobile network (PLMN) in a defined geographic area, and wherein the defined geographic area includes the PLMN and a distinct PLMN.

11. The method of any preceding clause, further comprising:
   determining a number of EC restrictions for the PLMN;
   determining an EC restriction outcome for the PLMN based on the number of EC restrictions for the PLMN; and
   setting the duration of the NAS timer according to the EC restriction outcome.

12. The method of any preceding clause, wherein the EC restriction outcome corresponds to a likelihood of EC restriction by the PLMN based on past EC restrictions of the distinct PLMN sharing the geographic area.

13. The method of any preceding clause, wherein the EC restriction corresponds to an enhanced coverage.

14. The method of any preceding clause, wherein the access request message corresponds to one of:
   an attached request message,
   an authentication response message,
   an authentication failure message,
   a tracking area update (TAU) request message,
   a registration for mobility message, or
   an initial registration request message.

15. An apparatus for wireless communication, comprising:
   a transceiver;
   a memory configured to store instructions; and
   at least one processor communicatively coupled with the transceiver and the memory, wherein the one or more processors are configured to execute the instructions to:
      determine operation in a wideband and support of an extended coverage (EC) restriction;

identify a duration of a non-access stratum (NAS) timer based on determining operation in the wideband and the EC restriction;

transmit an access request message to a network entity to trigger a mobility management procedure;

receive an acceptance message from the network entity indicating an unrestricted or restricted status of the EC restriction;

apply the duration to the NAS timer based on the acceptance message indicating the unrestricted or restricted status of the EC restriction received from the network entity or a history of EC restrictions of a public land mobile network (PLMN) in a defined geographic area; and initiate the NAS timer according to the identified duration.

16. The apparatus of any preceding clause, further comprising applying an initial duration of the NAS timer corresponding to a configured length of time set by the UE without an indication from the network entity of the EC restriction prior to receiving the acceptance message from the network entity, and wherein the initial duration is smaller than the identified duration.

17. The apparatus of any preceding clause, wherein the EC restriction corresponds to an EC Mode B restriction.

18. The apparatus of any preceding clause, wherein the duration of the NAS timer is set to a value corresponding to an indication of the EC restriction.

19. The apparatus of any preceding clause, wherein the duration of the NAS timer corresponds to a timer value between 5 and 15 seconds.

20. The apparatus of any preceding clause, wherein the duration of the NAS timer is set between a value corresponding to an indication of the EC restriction and a value corresponding to an indication of an unrestricted EC.

21. The apparatus of any preceding clause, wherein the duration of the NAS timer corresponds to a timer value between 15 seconds and 85 seconds.

22. The apparatus of any preceding clause, wherein the duration of the NAS timer is set to a value corresponding to an indication of an unrestricted EC.

23. The apparatus of any preceding clause, wherein the duration of the NAS timer corresponds to 85 seconds.

24. The apparatus of any preceding clause, wherein the duration of the NAS timer is based on past EC restrictions of a public land mobile network (PLMN) in a defined geographic area, and wherein the defined geographic area includes the PLMN and a distinct PLMN.

25. The apparatus of any preceding clause, further comprising:
determining a number of EC restrictions for the PLMN;
determining an EC restriction outcome for the PLMN based on the number of EC restrictions for the PLMN; and
setting the duration of the NAS timer according to the EC restriction outcome.

26. The apparatus of any preceding clause, wherein the EC restriction outcome corresponds to a likelihood of EC restriction by the PLMN based on past EC restrictions of the distinct PLMN sharing the geographic area.

27. The apparatus of any preceding clause, wherein the EC restriction corresponds to an enhanced coverage.

28. The apparatus of any preceding clause, wherein the access request message corresponds to one of:
an attached request message,
an authentication response message,
an authentication failure message,
a tracking area update (TAU) request message,
a registration for mobility message, or
an initial registration request message.

29. An apparatus for wireless communication, comprising means for
means for determining operation in a wideband and support of an extended coverage (EC) restriction;
means for identifying a duration of a non-access stratum (NAS) timer based on determining operation in the wideband and the EC restriction;
means for transmitting an access request message to a network entity to trigger a mobility management procedure;
means for receiving an acceptance message from the network entity indicating an unrestricted or restricted status of the EC restriction;
means for applying the duration to the NAS timer based on the acceptance message indicating the unrestricted or restricted status of the EC restriction received from the network entity or a history of EC restrictions of a public land mobile network (PLMN) in a defined geographic area; and
means for initiating the NAS timer according to the identified duration.

30. A non-transitory computer-readable medium, comprising code executable by one or more processors to:
determine operation in a wideband and support of an extended coverage (EC) restriction;
identify a duration of a non-access stratum (NAS) timer based on determining operation in the wideband and the EC restriction;
transmit an access request message to a network entity to trigger a mobility management procedure;
receive an acceptance message from the network entity indicating an unrestricted or restricted status of the EC restriction;
apply the duration to the NAS timer based on the acceptance message indicating the unrestricted or restricted status of the EC restriction received from the network entity or a history of EC restrictions of a public land mobile network (PLMN) in a defined geographic area; and
initiate the NAS timer according to the identified duration.

31. An apparatus for wireless communication, comprising:
means for determining operation in a wideband and support of an extended coverage (EC) restriction;
means for identifying a duration of a non-access stratum (NAS) timer based on determining the operation in the wideband and the EC restriction;
means for transmitting an access request message to a network entity to trigger a mobility management procedure;
means for receiving an acceptance message from the network entity indicating an unrestricted or restricted status of the EC restriction;
means for applying the duration to the NAS timer based on the acceptance message indicating the unrestricted or restricted status of the EC restriction received from the network entity or a history of EC restrictions of a public land mobile network (PLMN) in a defined geographic area; and
means for initiating the NAS timer according to the identified duration.

32. The apparatus of clause 31, wherein the duration of the NAS timer corresponds to a configured length of time set by the UE without an indication from the network entity of the EC restriction.

33. The apparatus of any preceding clause, wherein the EC restriction corresponds to an EC Mode B restriction.

34. The apparatus of any preceding clause, wherein the duration of the NAS timer is set to a value corresponding to an indication of the EC restriction.

35. The apparatus of any preceding clause, wherein the duration of the NAS timer corresponds to a timer value between 5 and 15 seconds.

36. The apparatus of any preceding clause, wherein the duration of the NAS timer is set between a value corresponding to an indication of the EC restriction and a value corresponding to an indication of an unrestricted EC.

37. The apparatus of any preceding clause, wherein the duration of the NAS timer corresponds to a timer value between 15 seconds and 85 seconds.

38. The apparatus of any preceding clause, wherein the duration of the NAS timer is set to a value corresponding to an indication of an unrestricted EC.

39. The apparatus of any preceding clause, wherein the duration of the NAS timer corresponds to 85 seconds.

40. The apparatus of any preceding clause, wherein the duration of the NAS timer is based on past EC restrictions of a public land mobile network (PLMN) in a defined geographic area, and wherein the defined geographic area includes the PLMN and a distinct PLMN.

41. The apparatus of any preceding clause, further comprising:
    means for determining a number of EC restrictions for the PLMN;
    means for determining an EC restriction outcome for the PLMN based on the number of EC restrictions for the PLMN; and
    means for setting the duration of the NAS timer according to the EC restriction outcome.

42. The apparatus of any preceding clause, wherein the EC restriction outcome corresponds to a likelihood of EC restriction by the PLMN based on past EC restrictions of the distinct PLMN sharing the geographic area.

43. The apparatus of any preceding clause, wherein the EC restriction corresponds to an enhanced coverage.

44. The apparatus of any preceding clause, wherein the access request message corresponds to one of:
    an attached request message,
    an authentication response message,
    an authentication failure message,
    a tracking area update (TAU) request message,
    a registration for mobility message, or
    an initial registration request message.

45. A non-transitory computer-readable medium including stored instructions of communications, executable by a processor to:
    determine operation in a wideband and support of an extended coverage (EC) restriction;
    identify a duration of a non-access stratum (NAS) timer based on determining the operation in the wideband and the EC restriction;
    transmit an access request message to a network entity to trigger a mobility management procedure;
    receive an acceptance message from the network entity indicating an unrestricted or restricted status of the EC restriction;
    apply the duration to the NAS timer based on the acceptance message indicating the unrestricted or restricted status of the EC restriction received from the network entity or a history of EC restrictions of a public land mobile network (PLMN) in a defined geographic area; and
    initiate the NAS timer according to the identified duration.

46. The non-transitory computer-readable medium of clause 45, wherein the duration of the NAS timer corresponds to a configured length of time set by the UE without an indication from the network entity of the EC restriction.

47. The non-transitory computer-readable medium of any preceding clause, wherein the EC restriction corresponds to an EC Mode B restriction.

48. The non-transitory computer-readable medium of any preceding clause, wherein the duration of the NAS timer is set to a value corresponding to an indication of the EC restriction.

49. The non-transitory computer-readable medium of any preceding clause, wherein the duration of the NAS timer corresponds to a timer value between 5 and 15 seconds.

50. The non-transitory computer-readable medium of any preceding clause, wherein the duration of the NAS timer is set between a value corresponding to an indication of the EC restriction and a value corresponding to an indication of an unrestricted EC.

51. The non-transitory computer-readable medium of any preceding clause, wherein the duration of the NAS timer corresponds to a timer value between 15 seconds and 85 seconds.

52. The non-transitory computer-readable medium of any preceding clause, wherein the duration of the NAS timer is set to a value corresponding to an indication of an unrestricted EC.

53. The non-transitory computer-readable medium of any preceding clause, wherein the duration of the NAS timer corresponds to 85 seconds.

54. The non-transitory computer-readable medium of any preceding clause, wherein the duration of the NAS timer is based on past EC restrictions of a public land mobile network (PLMN) in a defined geographic area, and wherein the defined geographic area includes the PLMN and a distinct PLMN.

55. The non-transitory computer-readable medium of any preceding clause, further comprising instructions to:
    determine a number of EC restrictions for the PLMN;
    determine an EC restriction outcome for the PLMN based on the number of EC restrictions for the PLMN; and
    setting the duration of the NAS timer according to the EC restriction outcome.

56. The non-transitory computer-readable medium of any preceding clause, wherein the EC restriction outcome corresponds to a likelihood of EC restriction by the PLMN based on past EC restrictions of the distinct PLMN sharing the geographic area.

57. The non-transitory computer-readable medium of any preceding clause, wherein the EC restriction corresponds to an enhanced coverage.

58. The non-transitory computer-readable medium of any preceding clause, wherein the access request message corresponds to one of:
    an attached request message,
    an authentication response message,
    an authentication failure message,
    a tracking area update (TAU) request message,
    a registration for mobility message, or
    an initial registration request message.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single-or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium. The processes of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper orientation of any device as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A method of wireless communication at a user equipment (UE), comprising:
   identifying operation in a wideband and support of an extended coverage (EC) restriction;
   identifying a duration of a non-access stratum (NAS) timer based on identifying the operation in the wideband and support of the EC restriction;
   transmitting an access request message to a network entity to trigger a mobility management procedure;

receiving an acceptance message from the network entity indicating an unrestricted or restricted status of the EC restriction;

applying the duration to the NAS timer based at least in part on a history of EC restrictions of a public land mobile network (PLMN) in a defined geographic area; and initiating the NAS timer according to the identified duration.

2. The method of claim 1, further comprising applying an initial duration of the NAS timer corresponding to a configured length of time set by the UE without an indication from the network entity of the EC restriction prior to receiving the acceptance message from the network entity, and wherein the initial duration is smaller than the identified duration.

3. The method of claim 1, wherein the EC restriction corresponds to an EC Mode B restriction.

4. The method of claim 1, wherein the duration of the NAS timer is set to a value corresponding to an indication of the EC restriction.

5. The method of claim 4, wherein the duration of the NAS timer corresponds to a timer value between 5 and 15 seconds.

6. The method of claim 1, wherein the duration of the NAS timer is set between a value corresponding to an indication of the EC restriction and a value corresponding to an indication of an unrestricted EC.

7. The method of claim 6, wherein the duration of the NAS timer corresponds to a timer value between 15 seconds and 85 seconds.

8. The method of claim 1, wherein the duration of the NAS timer is set to a value corresponding to an indication of an unrestricted EC.

9. The method of claim 8, wherein the duration of the NAS timer corresponds to 85 seconds.

10. The method of claim 1, wherein the duration of the NAS timer is based on the history of EC restrictions of the PLMN in the defined geographic area, and wherein the defined geographic area includes the PLMN and a distinct PLMN.

11. The method of claim 10, further comprising:
identifying a number of EC restrictions for the PLMN;
identifying an EC restriction outcome for the PLMN based on the number of EC restrictions for the PLMN; and
setting the duration of the NAS timer according to the EC restriction outcome.

12. The method of claim 11, wherein the EC restriction outcome corresponds to a likelihood of EC restriction by the PLMN based on past EC restrictions of the distinct PLMN sharing the geographic area.

13. The method of claim 1, wherein the EC restriction corresponds to an enhanced coverage.

14. The method of claim 1, wherein the access request message corresponds to one of:
an attached request message,
an authentication response message,
an authentication failure message,
a tracking area update (TAU) request message,
a registration for mobility message, or
an initial registration request message.

15. An apparatus for wireless communication, comprising:
a transceiver;
a memory configured to store instructions; and
at least one processor communicatively coupled with the transceiver and the memory, wherein the one or more processors are configured to execute the instructions to:
identify operation in a wideband and support of an extended coverage (EC) restriction;
identify a duration of a non-access stratum (NAS) timer based on identifying operation in the wideband and support of the EC restriction;
transmit an access request message to a network entity to trigger a mobility management procedure;
receive an acceptance message from the network entity indicating an unrestricted or restricted status of the EC restriction;
apply the duration to the NAS timer based at least in part on a history of EC restrictions of a public land mobile network (PLMN) in a defined geographic area; and
initiate the NAS timer according to the identified duration.

16. The apparatus of claim 15, further comprising applying an initial duration of the NAS timer corresponding to a configured length of time set by the UE without an indication from the network entity of the EC restriction prior to receiving the acceptance message from the network entity, and wherein the initial duration is smaller than the identified duration.

17. The apparatus of claim 15, wherein the EC restriction corresponds to an EC Mode B restriction.

18. The apparatus of claim 15, wherein the duration of the NAS timer is set to a value corresponding to an indication of the EC restriction.

19. The apparatus of claim 18, wherein the duration of the NAS timer corresponds to a timer value between 5 and 15 seconds.

20. The apparatus of claim 15, wherein the duration of the NAS timer is set between a value corresponding to an indication of the EC restriction and a value corresponding to an indication of an unrestricted EC.

21. The apparatus of claim 20, wherein the duration of the NAS timer corresponds to a timer value between 15 seconds and 85 seconds.

22. The apparatus of claim 15, wherein the duration of the NAS timer is set to a value corresponding to an indication of an unrestricted EC.

23. The apparatus of claim 22, wherein the duration of the NAS timer corresponds to 85 seconds.

24. The apparatus of claim 15, wherein the duration of the NAS timer is based on the history of EC restrictions of the PLMN in the defined geographic area, and wherein the defined geographic area includes the PLMN and a distinct PLMN.

25. The apparatus of claim 24, further comprising:
determine a number of EC restrictions for the PLMN;
determine an EC restriction outcome for the PLMN based on the number of EC restrictions for the PLMN; and
set the duration of the NAS timer according to the EC restriction outcome.

26. The apparatus of claim 25, wherein the EC restriction outcome corresponds to a likelihood of EC restriction by the PLMN based on past EC restrictions of the distinct PLMN sharing the geographic area.

27. The apparatus of claim 15, wherein the EC restriction corresponds to an enhanced coverage.

28. The apparatus of claim 15, wherein the access request message corresponds to one of:
an attached request message,
an authentication response message, an authentication failure message,
a tracking area update (TAU) request message,
a registration for mobility message, or
an initial registration request message.

29. An apparatus for wireless communication, comprising:
- means for identifying operation in a wideband and support of an extended coverage (EC) restriction;
- means for identifying a duration of a non-access stratum (NAS) timer based on identifying operation in the wideband and support of the EC restriction;
- means for transmitting an access request message to a network entity to trigger a mobility management procedure;
- means for receiving an acceptance message from the network entity indicating an unrestricted or restricted status of the EC restriction;
- means for applying the duration to the NAS timer based at least in part on a history of EC restrictions of a public land mobile network (PLMN) in a defined geographic area; and
- means for initiating the NAS timer according to the identified duration.

30. A non-transitory computer-readable medium, comprising code executable by one or more processors to:
- identify operation in a wideband and support of an extended coverage (EC) restriction;
- identify a duration of a non-access stratum (NAS) timer based on identifying operation in the wideband and support of the EC restriction;
- transmit an access request message to a network entity to trigger a mobility management procedure;
- receive an acceptance message from the network entity indicating an unrestricted or restricted status of the EC restriction;
- apply the duration to the NAS timer based at least in part on a history of EC restrictions of a public land mobile network (PLMN) in a defined geographic area; and
- initiate the NAS timer according to the identified duration.

* * * * *